United States Patent [19]

Metz-Stavenhagen et al.

[11] Patent Number: 5,468,241

[45] Date of Patent: Nov. 21, 1995

[54] SUPPORT DEVICE FOR THE HUMAN VERTEBRAL COLUMN

[75] Inventors: Peter Metz-Stavenhagen, Bad Wildungen; Klaus F. A. Behrens, Rickling, both of Germany

[73] Assignee: Howmedica GmbH, Schoenkirchen, Germany

[21] Appl. No.: 195,895

[22] Filed: Feb. 10, 1994

Related U.S. Application Data

[63] Continuation of Ser. No. 875,578, Apr. 27, 1992, abandoned, which is a continuation of Ser. No. 735,203, Jul. 24, 1991, abandoned, which is a continuation of Ser. No. 579,212, Sep. 5, 1990, abandoned, which is a continuation of Ser. No. 313,404, Feb. 21, 1989, abandoned.

[30] Foreign Application Priority Data

Feb. 18, 1988 [DE] Germany .................. 8802112 U

[51] Int. Cl.[6] ................................ A61B 17/56
[52] U.S. Cl. ............................ 606/61; 606/73
[58] Field of Search ............... 606/53–61, 105; 623/16, 17

[56] References Cited

U.S. PATENT DOCUMENTS

| | | | |
|---|---|---|---|
| 4,047,523 | 9/1977 | Hall | 606/61 |
| 4,257,409 | 3/1981 | Bacal | 606/61 |
| 4,361,141 | 11/1982 | Tanner | 606/61 |
| 4,382,438 | 5/1983 | Jacobs | 606/61 |
| 4,404,967 | 9/1983 | Bacal et al. | 606/61 |
| 4,433,677 | 2/1984 | Ulrich et al. | 606/61 |
| 4,448,191 | 5/1984 | Rodnyansky et al. | 606/61 |
| 4,611,580 | 9/1986 | Wu | 606/61 |
| 4,641,636 | 2/1987 | Cotrel | 606/61 |
| 4,653,481 | 3/1987 | Howland et al. | 606/61 |
| 4,658,809 | 4/1987 | Ulrich et al. | 606/61 |
| 4,987,892 | 1/1991 | Krag et al. . | |

FOREIGN PATENT DOCUMENTS

| | | |
|---|---|---|
| 3121272 | 12/1982 | Germany . |
| 3306657 | 12/1986 | Germany . |
| 3624067 | 2/1987 | Germany . |
| 3614101 | 10/1987 | Germany . |
| 8711317 | 12/1987 | Germany . |
| 3219575 | 2/1988 | Germany . |

*Primary Examiner*—Michael A. Brown
*Attorney, Agent, or Firm*—Peter C. Richardson; Lawrence C. Akers; Elizabeth O. Slade

[57] ABSTRACT

Support device for the human vertebral column having an elongated dorsally implantable holding device, at least two pedicle screws which have a head and a threaded shank and the head of which is mounted on the holding device pivotally about an axis which extends approximately perpendicularly to the threaded shank axis whilst the threaded shank projects from the holding device, and a securing device for the fixing of the pedicle screws in the set angular position and at desired axial intervals from each other, wherein the holding device includes at least two separate preferably threaded bolts which cooperate with a preferably threaded sleeve and which at the head ends includes a clamping surface lying on the axis or axis-parallel, the head of the pedicle screws includes two approximately parallel clamping faces extending approximately parallel to the threaded shank axis and for each bolt a screw connection is provided which clampingly fixes with respect to each other in their position the clamping surfaces of bolts and pedicle screws or of two bolts.

29 Claims, 3 Drawing Sheets

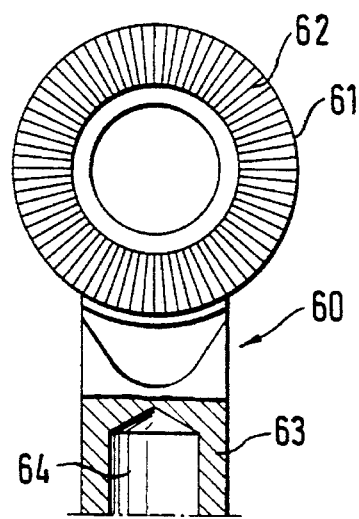
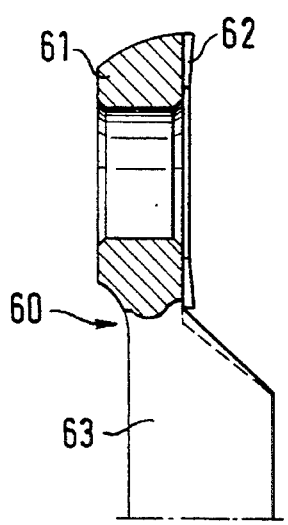
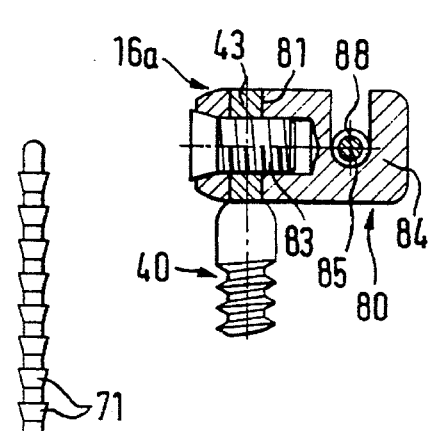
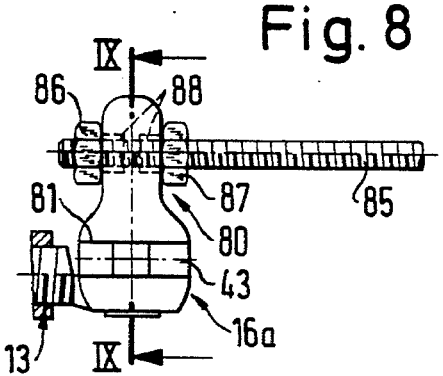
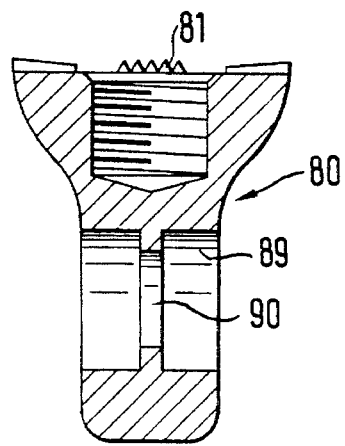

SUPPORT DEVICE FOR THE HUMAN VERTEBRAL COLUMN

This is a continuation, of application Ser. No. 07/875,578, filed on Apr. 27, 1992, now abandoned, which in turn is a continuation of application Ser. No. 07/735,208, filed Jul. 24, 1991, now abandoned, which in turn is a continuation of application Ser. No. 07/579,212 filed Sep. 5, 1990, now abandoned, which in turn is a continuation of application Ser. No. 07/313,404, filed Feb. 21, 1989, now abandoned.

BACKGROUND OF THE INVENTION

The invention relates to a support device for the human vertebral column.

DE-GM 8,711,317 discloses a support device for the vertebrae of the human vertebral column in which so-called Schanz screws are screwed via the pedicles into the vertebra body. Said screws are received in holding bushes which are mounted rotatably in holding bodies. The holding bodies in turn can be screwed onto the end of a threaded bolt. The known supporting device permits an adjustment of the Schanz screws in three degrees of freedom; it can therefore not only be screwed at the correct angle into the arch foot but also permits thereafter a free movement in space in order for example to adjust two vertebrae with respect to each other in a desired manner. This is for example necessary to carry out a reduction of vertebrae and/or relieve a fractured vertebra from the adjacent vertebrae. However, the known support device is not able to bridge more than one vertebra or to ensure a multisegmentary repair for instance in the case of so-called layered or multilevel fractures.

It is also already known to fix pedicle screws to a thread wire. The pedicle screws have a forked head which comprises two cylindrical bore portions which are spaced by a web and open towards the fork opening and into which the cylinder portions have nuts which are screwed onto the thread wire can be introduced. With the aid of two nuts a pedicle screw can be fixed both in the axis position on the wire and in its rotational position on the thread or screw wire. With the aid of such a support device, in which the thread wire is implanted dorsally, pedicle screws can be set in a number of vertebrae. However, because of inadequate strength the known support device does not provide any primarily stable support. It can therefore essentially be used only for vertical columns which are in themselves stable and the line of which is to be corrected for orthopaedic reasons. The known device is not suitable for a repair of vertebral column fractures, in particular multilevel or layered fractures.

The innovation is therefore based on the problem of providing a support device for the human vertebral column with which more than one vertebra can be bridged and which permits a primary stabilization of the vertebrae with respect to all degrees of freedom.

This problem is solved according to the invention by the features of the apparatus of the invention.

SUMMARY OF THE INVENTION

The device according to the invention comprises at least two separate preferably threaded bolts which cooperate with a preferably threaded sleeve. The head ends of the bolts are provided with a clamping face which is disposed co-axially or axis-parallel. With the aid of a suitable securing means any desired number of bolt pairs connected by the sleeve can be connected together, the clamping face of a bolt pair being brought into clamping engagement with a clamping face of the adjacent bolt pair. The pedicle screws in turn have clamping faces and are fixed with the aid of a securing means to a clamping face of a bolt head or between the clamping faces of interconnected bolt heads. The ends of a bolt pair connected via the sleeve thus form the attachment points for the pedicle screw. By varying the axial spacing of the bolts with respect to each other, for example with the aid of a threaded sleeve, the attachment points can thus be adjusted. At the same time the bolts permit a rotation of the pedicle screws about the axis of the bolts through a desired angle. In addition the pedicle screws can be pivoted about an axis perpendicular to their axis with respect to the connecting points and fixed in the assumed position. The pedicle screw can thus assume any desired position in space and be locked in said position.

With the support device according to the invention the pedicle screws can thus be screwed into any desired vertebra and fixed desired vertebrae of a vertebral column section with respect to each other. The support device according to the invention is therefore suitable for a primary stabilizing of the vertebral column, for instance in the case of fractures of one or more vertebrae. The interconnected bolts forming a holding means can be made stable enough to ensure the desired force absorption and relieve for instance fractured vertebrae. The support device according to the invention is therefore suitable also for correction of vertebral column sections of greater or lesser length.

To obtain as effective as possible a locking of the bolt pairs with respect to each other and of the pedicle screws with respect to the bolt heads the clamping faces have the highest possible roughness to achieve a high force locking. Alternatively, according to a preferred embodiment of the invention the clamping faces may have a toothing. The toothing permits a stepwise adjustment of the clamping faces with respect to each other in the minimum spacing of one tooth spacing which will however probably be fully sufficient for most cases encountered. Above all however a form locking is achieved by which a high securing against turning is ensured.

As already mentioned the clamping faces are pressed against each other with the aid of a screw connection. Preferably, a screw bolt is provided which extends through bores of the bolt heads and of the pedicle screws. The screw bolts preferably cooperate with a threaded bore in a bolt head, a second bolt head or the bore in the head of the pedicle screw having an internal cone which cooperates with the cone of the screw bolt head to ensure an effective force transmission. Such a construction further has the advantage that the screw bolt can be attached completely sunken and thus does not form a part which projects in troublesome manner.

As already mentioned, the spacing of the bolt heads can be adjusted via the threaded sleeve if the bolts have a thread. Said sleeve comprises according to a further development of the invention key or spanner faces. In this manner a considerable axial force can be applied for example to adjust two vertebrae relatively to each other. However, the sleeve serves primarily to adapt the bolt heads to the particular dimensions of the vertebrae.

To fix the assumed position of the bolt heads with respect to each other as well as their axial spacing suitable locking means are provided. They consist according to a further development of the invention in that a lock nut is screwed onto the threaded shank of a bolt. The lock nut secures the rotational position of the bolt relatively to the threaded sleeve and thus also the axial position thereof. Alternatively or additionally, the threaded sleeve can be provided with two lock screws to fix said sleeve non-rotatably with respect to the threaded shank of the threaded bolts.

Another possibility of locking the sleeve with respect to the bolts resides according to a further development of the invention in that a sleeve deformable by squeezing is provided. Once the spacing of the bolt heads has been correctly set the sleeve can be squeezed onto the bolts and according to another embodiment of the invention cooperates with flattenings at the bolt ends to obtain an effective securing against rotation. With the aid of collars or grooves axial securing can also be achieved by squeezing. A sleeve adapted to be squeezed on can be formed both as threaded sleeve or as smooth sleeve in order to provide a connection between the bolts and a subsequent locking. If the sleeve is not provided with a thread it can be fixedly connected to one bolt from the start so that only a relative movement between the other bolt and the sleeve is possible and consequently a squeeze or squash connection need only be made with the movable bolt.

In an alternative embodiment of the invention the sleeve is at least partially split and a clamping means is associated with the sleeve for clamping the sleeve fixedly on at least one bolt. In this case the sleeve is constructed as clamping ring or a sort of clip which with the aid of a clamping means, for example a screw connection, can be secured clampingly on one or both bolts.

A particularly effective securing against rotation is obtained in that the threaded bolt has at least one flattening. On the threaded bolt a washer is mounted which due to the flattening is non-rotatable but is axially displaceable. The washer comprises an end-face toothing comparable to the toothing for the pedicle screw already described. A corresponding toothing is also provided at the end face of the sleeve. With the aid of the lock nut the washer or disc is pressed against the sleeve. In this manner a double securing against rotation is obtained. The one securing takes place between the washer and the threaded sleeve and the second between the lock nut and the washer.

As support device for the vertebral column a so-called Harrington rod is known which can be attached at one end to a vertebra of the vertebral column and which in the other end region permits a stepwise adjustment of a holding member which is connectable to another vertebra. The support device according to the invention can also be combined with such a rod. In this connection a further development of the invention provides that at least one separate elongated bolt is provided having a head with a clamping face and holding means at the other end for a connecting member to be attached to a vertebra. In this embodiment for example the Harrington rod comprises at the end opposite the holding means an eye having a clamping face according to the invention. In another embodiment of the invention the bolt shank comprises a blind bore into which the cylindrical pin of an elongated rod, for example a Harrington rod, can be inserted. A withdrawal securing need not be provided because such a support device is usually subjected to compressive load.

A third alternative provides that the already repeatedly mentioned sleeve is provided with an insert bore for receiving a preferably cylindrical pin of an elongated rod, for example a Harrington rod.

Hooks which have a through bore in a holding portion can also be combined with a Harrington rod or the like. With the aid of a locking screw a hook can be fixed in any desired position on the rod or bar. The hook may for example be a so-called lamina hook which engages beneath the lamina of a vertebra. It may however also be a pedicle hook which is preferably made fork-like at the free end. A lower lamina hook may likewise be provided with a clamping face which cooperates with the clamping face of the elongated rod. The pedicle hook may additionally be equipped with a tab to fix it to a vertebra body with the aid of bone screws. Two rods extending adjacent to but spaced from each other may be clamped together with the aid of double hooks, the double hooks being adjustable to a desired distance apart with the aid of suitable means.

As already mentioned, it is known to fix pedicle screws with the aid of nuts on a threaded rod. The support device according to the invention can also be combined with the known support device. For this purpose a further development of the invention provides an adapter which comprises at one end a clamping face for connection with a bolt or a pedicle screw by means of the screw connection. The adapter further comprises a fork portion spaced from the clamping face for receiving an elongated preferably threaded rod in a plane approximately parallel to the plane drawn through the adjacent pedicle screw, the rod preferably being lockable on the adapter by means of nuts. In this embodiment the axis of the rod is laterally offset with respect to the bolt axis. This lateral offsetting is however not critical.

BRIEF DESCRIPTION OF THE DRAWINGS

The invention will be explained in detail hereinafter with the aid of an example of embodiment illustrated in the drawings.

FIG. 5 shows a side view of a pluggable bolt.

FIG. 6 shows a side view of the bolt of FIG. 5 turned through 90°.

FIG. 7 shows a longer rod-like bolt which is formed as Harrington rod.

FIG. 8 shows the plan view of a connection of a bolt with a conventional threaded rod.

FIG. 9 shows a section through the illustration of FIG. 8 along the line 9—9 turned through 90°.

FIG. 10 shows a section through the adapter shown in FIGS. 8 and 9.

DETAILED DESCRIPTION OF THE DRAWINGS

Figure 1:
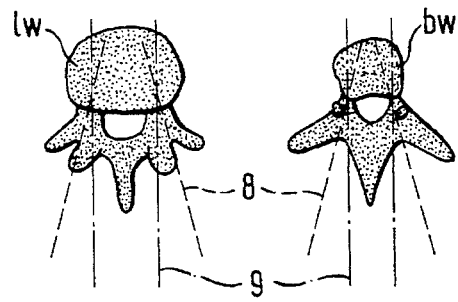
FIG. 1 shows a plan view of a schematically illustrated lumbar vertebra and a thoracic vertebra.

FIG. 1 shows a lumbar vertebra lw and a thoracic vertebra bw in schematic plan view. The dashed lines 10 indicate axes of bores which are formed to receive pedicle screws. The bores extend between the processus spinosus and transverse process or costal process through the vertebral arch foot (pedicle) into the vertebra body. Axes in dot-dash line for bores through the pedicles into the vertebra body as may be provided for receiving pedicle screws.

Figure 2:
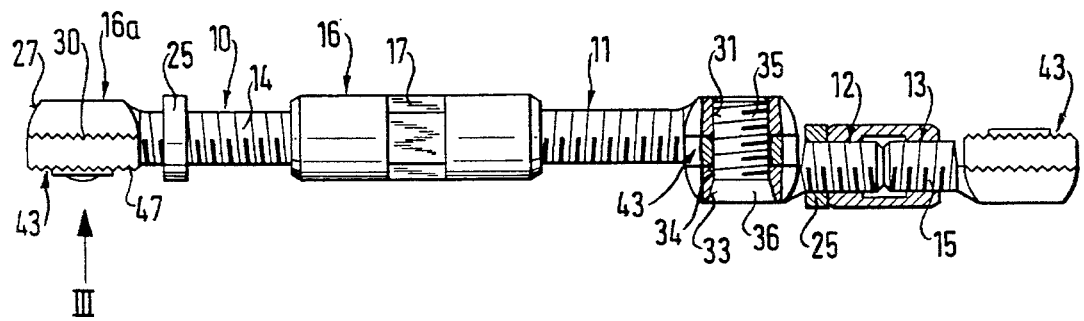
FIG. 2 shows a plan view partially in section of the support device according to the invention.
Figure 3:
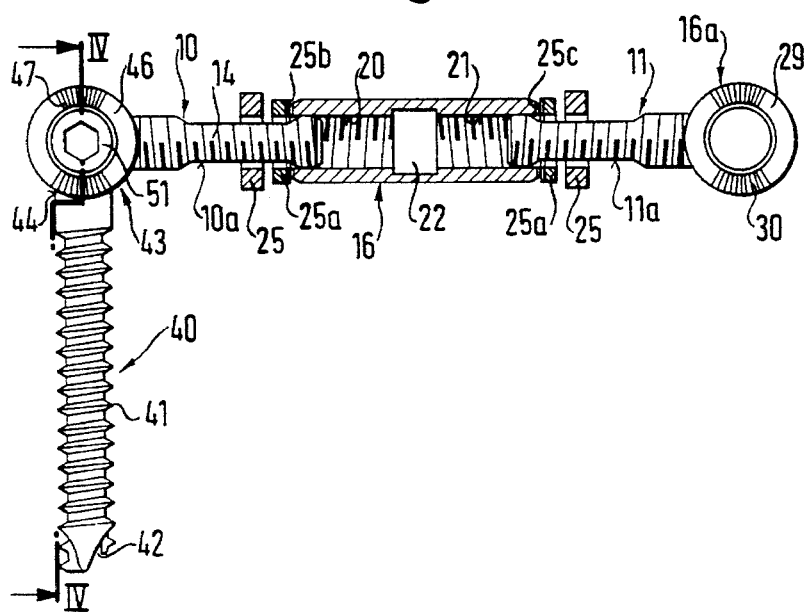
FIG. 3 shows a view of the support device according to FIG. 2 in the direction of the arrow 3 but with a special securing against rotation.
Figure 4:
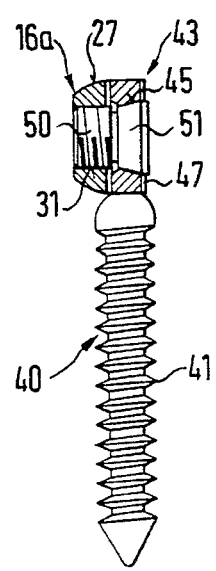
FIG. 4 shows a section through the illustration of FIG. 3 along the line 4—4.

The support device illustrated in FIGS. 2 to 4 comprises threaded bolts 10, 11 and 12, 13. They are arranged in pairs and have a threaded shank 14 and 15 and a head 16a. As can be seen the threaded shank 14 of the threaded bolts 10, 11 is longer than the threaded shank 15 of the threaded bolts 12, 13. The head 16a is of the same dimensions from the outside for all threaded bolts. The threaded shanks 14 of the threaded bolts 10, 11 are connectable together via a threaded sleeve 16. The threaded sleeve 16 is provided in the centre with a hexagon 17 forming the spanner or key faces. The threaded sleeve 16 comprises two threaded bore portions 20, 21 which have oppositely running threads. Therebetween there is a relief bore portion 22 of enlarged diameter. By turning the threaded sleeve 16 the threaded bolts 10, 11 can be varied in their axial spacing from each other.

On the threaded shank 14 of the threaded bolt 10 in FIG. 2 there is a lock nut 25 which can be engaged against the associated end face of the threaded sleeve. It is clear that a lock nut may also be disposed on the threaded shank of the threaded bolt 11.

In the modified embodiment of FIG. 3 the shanks 14 of the threaded bolts 10, 11 are provided with diametrically opposite flattenings 10a, 11a. On the threaded bolts 10, 11 discs or washers 25a are mounted whose opening is adapted to the cross-section of the threaded bolts 10, 11. They can therefore be axially displaced but not turned relatively to the threaded bolt. The washers 25a have at an end side a toothing 25b corresponding to the heads 16a of the threaded bolts (the toothing will be discussed in detail below). The ends of the threaded sleeve 16 are provided with a corresponding toothing 25c which cooperates with the toothing 25b to prevent the threaded sleeve from turning with respect to the washer 25b.

The configuration of the head 16a of the threaded bolts is annular and slightly outwardly spherical as shown at 27. On the larger diameter side of the annular head 16 an annular clamping face 29 is provided which is formed substantially by a toothing 30. As apparent in FIG. 2 the head of the threaded bolt 11 comprises a threaded bore 31. The head of the threaded bolt 12 however comprises a conical bore portion 33 which is followed by a cylindrical bore portion 34. The portions described accommodate a screw bolt 35 which has a conical head 36 which cooperates with the conical bore portion 33 of the threaded bolt 12.

The support device shown also comprises pedicle screws of which one is shown at 40 in FIGS. 3 and 4. The pedicle screw 40 comprises a threaded shank 41 with a self-cutting thread which has a cutting groove 42 at the tip. The thread leaves free a smooth cylindrical portion 44 near the annular head 43. As apparent in FIGS. 2 and 4 the bore 43 of the pedicle screw 40 comprises a double-cone bore 45. On both sides annular clamping faces 46 are provided and are formed by a toothing 47. The toothing 47 cooperates with the toothing 30 of the clamping faces 29 of the heads 16a of the threaded bolts 10 to 13. FIG. 2 shows how the head 43 of a pedicle screw 40 is clamped between two clamping faces 49 of the heads 16a of two adjacent threaded bolts 10 and 11, this being done with the aid of the screw bolt 35. FIGS. 3 and 4 show how a pedicle screw 40 is fixedly clamped against a head 16a of the threaded bolt 11 with the aid of a screw bolt 50 having a conical head 51. The threaded bolt 50, which can also be attached completely sunken, is similar in appearance to the threaded bolt 35 but is shorter than the latter. The head of the threaded bolts comprises inner sunken spanner faces, for example an inner hexagon to effect the desired screwing.

The pedicle screws 40 are inserted in the manner described above into the desired vertebra. With the aid of the longer threaded bolts 10, 11 it is possible to connect two vertebrae spaced one vertebra apart or to support them with respect to each other; the exact spacing can be set with the aid of the threaded sleeve 16. The threaded bolts 12, 13 permit on the other hand a connection of two adjacent vertebrae with the aid of screwed-in pedicle screws 40. As can be seen the rotational position about the bore axis of the head 43 of the pedicle screws 40 can be varied in the interval of the teeth of the toothing 47. The variation of the rotational position of the pedicle screws 40 perpendicular thereto can be effected by turning the associated threaded bolts 10, 11, 12, 13. The spacing of adjacent pedicle screws can be adjusted via the threaded sleeve 16. Consequently, by the pressing together of the clamping faces and the locking of the threaded sleeve 16 with the aid of the lock nuts 25 or the washers 25a any desired position of the pedicle screws 40 in space may be defined. This applies for each pedicle screw which is attached in the chain of adjacent threaded bolt pairs. Obviously, two such chains must be provided along with the vertebral column or a vertebra section.

The support device described is made in modular manner although interconnected heads of threaded bolts have different bores, one of which has a threaded bore and the other a conical bore portion. In contrast the pedicle screws can be made identical for all threaded bolts.

In FIGS. 5 and 6 a bolt 60 is shown which comprises an annular head 61. The annular head 61 corresponds to the head 16a of FIGS. 2 to 4 with the following exceptions. Its toothed clamping face 62 is slightly conically disc shaped as apparent from FIG. 6 and lies approximately on the axis of the bolt shank 63. The bolt shank 63 comprises a blind bore 64. It serves for example to receive a cylindrical pin of an elongated rod, which is not shown, for example a Harrington rod.

FIG. 7 shows a modified Harrington rod 70 which is provided in an end region with a row of conical portions 71 which cooperate with an annular connecting member which is adapted to be attached to a vertebra. In the attachment the connecting piece slides along the conical portions 21 when the curved vertebral column is bent straight until it engages behind the last conical portion 71. At the other end the Harrington rod 70 comprises an annular head 72 which is identical to the head 61 of FIGS. 5 and 6 or the head 16a of FIGS. 2 to 4. There is therefore no need to describe the details again. By means of the head 72 a connection can therefore be made to a bolt 10 or 11 in accordance with FIGS. 2 to 4 with or without one of the pedicle screws illustrated in FIGS. 2 to 4.

In the embodiment according to FIGS. 8 and 9 the end of a bolt 13 is shown with the head 16a corresponding to the illustration of FIG. 2 in connection with a pedicle screw 40. On the opposite side of the head 43 of the pedicle screw 40 an adapter 80 is disposed which comprises a clamping face 81 which corresponds to the clamping faces 46 and 29 of the pedicle screw 40 or the bolt 11. The adapter 80 also comprises a blind bore for receiving a screw bolt 83 which is fundamentally the same as the screw bolt 35 according to FIG. 2, at least as regards the mode of action. The adapter 80 comprises a fork-like portion 84 which receives a threaded rod 85. The threaded rod 85 is somewhat smaller in diameter than the width of the fork gap. On the threaded rod 85 two nuts 86, 87 are mounted which comprise a cylindrical portion 88 having an outer diameter equal to the width of the gap of the fork portion 84. With the aid of the nuts 86, 87 the threaded rod 85 is locked in the fork portion 84. As can be seen from FIG. 10 the fork gap 89 may comprise a constriction 90, the constriction corresponding to the diameter of the threaded rod 85 whilst the remaining width, as already mentioned, corresponds to the diameter of the cylindrical portions 88 of the nuts 86, 87.

As can be seen in FIGS. 8 and 9 the axis of the thread rod 85 is somewhat offset with respect to the axis of the bolt 13. This offsetting is however not critical.

The pedicle screw 40 may have a conical core which tapers towards the free end.

Figure 11:
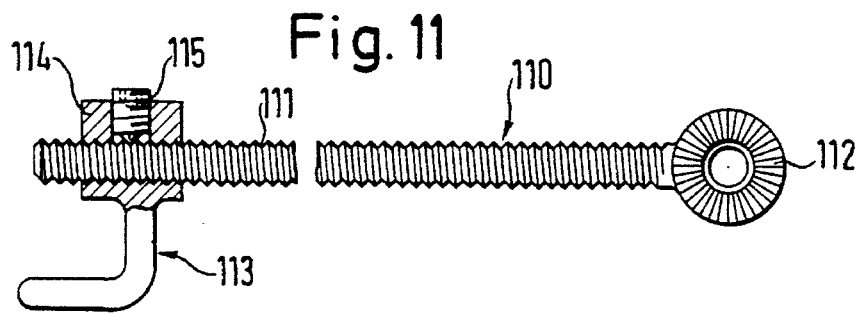
FIG. 11 shows a modified form of a Harrington rod with an upper lamina hook.

In FIG. 11 a traction rod according to FIG. 7 is shown. Its elongated shank 110 comprises a helically grooved surface 111. At one end an annular clamping head 112 is integrally formed having a radial toothing which has already been described in conjunction with the other Figures. A lamina hook 113 engaging beneath the lamina of a vertebra comprises a holding portion 114 having a through bore through which the shank 110 can be led. With the aid of a locking screw 115 which extends in a threaded bore transversely of the through bore of the holding portion 114 the hook 113 can be fixed at a desired axial position to the rod 110. The screw 115, constructed as grub screw with for example hexagon socket, can taper to a point at the lower end to cooperate with the thread-like surface 111. This prevents the hook 113 slipping on the rod 110. The clamping 112 may for example be secured to a lower vertebra in desired orientation with the aid of a pedicle screw.

Figure 12:
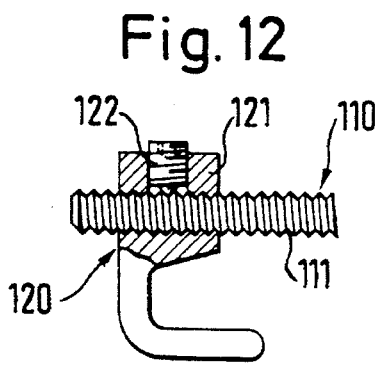
FIG. 12 shows the hook according to FIG. 11 in inverted arrangement on the rod.
Figure 13:
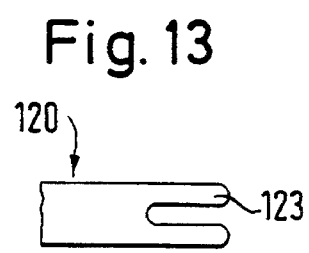
FIG. 13 shows a plan view of a part of the upper pedicle hook according to FIG. 12.

In FIG. 12 the end of the rod 110 according to FIG. 11 is shown. In this case it serves to receive an upper pedicle hook 120 which comprises a holding portion 121 having a threaded bore for receiving a locking screw 122. Whereas the hook opening of the lamina hook 113 points away from the clamping head 112 the hook opening of the pedicle hook 120 points in the same direction. The hook 120 engages round the pedicle of a vertebra. As shown in FIG. 13 it may be made fork-like, as indicated at 123, towards the free end.

Figure 14:
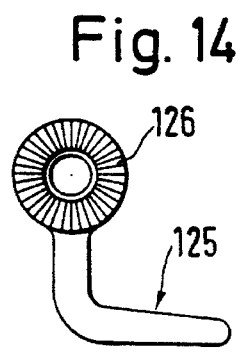
FIG. 14 shows a lower lamina hook for attaching to the clamping face of the rod according to FIG. 11.

FIG. 14 shows a lower lamina hook 125 which comprises a clamping head 126 at the end remote from the hook tip. The hook may for example be attached with the clamping head 112 of the rod 110 in the desired angular relationship. The different angular association permits a favourable anatomical adaptation and prevents the hook from slipping down the lamina of a lower vertebra, which would make reoperation necessary.

Figure 15:
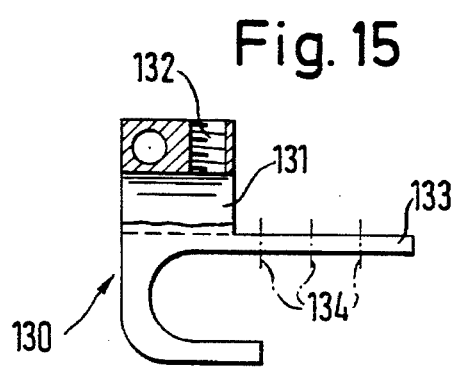
FIG. 15 shows an upper pedicle hook with additional tab or plate.

It is frequently necessary to brace with respect to each other two rod-like fixation elements which are led more or less parallel to the vertebral column. There is a danger that hooks connected conventionally to the rod will tear out. FIG. 15 shows a pedicle hook which withstands such a load. The pedicle hook 130 corresponds in its structure substantially to that of FIGS. 12 and 13. The rod 110 according to FIG. 11 is inserted through a bore 131 and a threaded bore 132 extending transversely thereof receives a locking screw to fix the hook 130 on the bar 110 in a desired axial position. In addition the hook 130 comprises parallel to the axis of the bore 131 a flat tab or plate 133 having two bores indicated merely by dot-dash lines 134. They serve to receive bone screws for additionally fixing the pedicle hook 130 on the vertebra body.

With the described hook and rods in desired manner a traction or compression can be carried out, depending on a particular situation.

Figure 17:
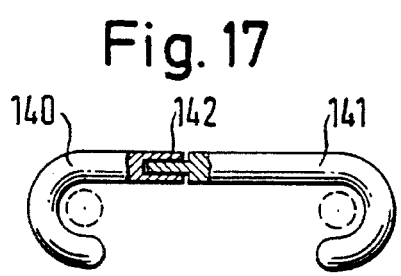
FIG. 17 shows another embodiment of a cross-connection hook.
Figure 19:
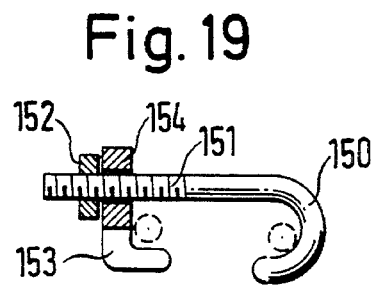
FIG. 19 shows a fourth embodiment of a cross-connection hook.

The examples of embodiment according to FIGS. 17 and 19 serve to exert a tensile stress between adjacently extending rods. In FIG. 17 two hook portions 140, 141 are telescopically inserted into each other as shown at 142. In this manner a double hook is formed of which each laterally engages round a rod as indicated in dashed line. In the connecting region 142, which is also adjustable in its axial position, a press deformation may be carried out to connect the two hook portions 140, 141 immovably to each other.

In FIG. 19 a hook portion 150 is provided whose holding portion 151 comprises a thread onto which a nut 152 is screwed. A second hook 153 comprises in a holding portion 154 a through bore through which the holding portion 151 of the hook 150 is led. The two hooks 150, 153 in turn can each laterally engage round a rod according to FIG. 11. With the aid of the nut 112 an additional adjustable tension can be applied between the rods.

Figure 16:
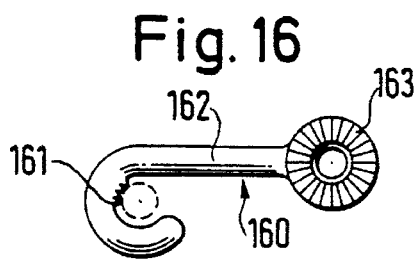
FIG. 16 shows a cross-connection hook.
Figure 18:
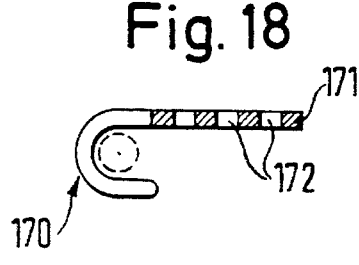
FIG. 18 shows a third embodiment of a cross-connection hook.

In the embodiment according to FIG. 16 a hook 160 comprises a toothing 161 for engaging for example a traction rod (shown in dashed line) to fix an axial position of the rod as well. Such a toothing may also be provided in other hooks as illustrated in FIGS. 17, 18 and 19. On the side opposite the hook on the holding portion 162 a clamping head 163 is formed which is comparable to the clamping head 112 for the rod 110 according to FIG. 11. The clamping head 163 is for example braced with a pedicle screw according to FIG. 4.

In the embodiment according to FIG. 18 a hook 170 is provided which has a rectilinear flat holding portion 171 which has a plurality of axially spaced bores 172 for securing the hook to a vertebra with the aid of bone screws. In its function it is comparable to the hook according to FIG. 16. Moreover, it may also be secured to a lamina or pedicle hook as illustrated in FIGS. 11, 12 or 15 via the holding portions with the aid of locking screws.

The modified traction rod illustrated above can not only be pushed by the lamina or pedicle screws but can also be inserted into the hooks and fixed with a correspondingly attached clamping means. This is necessary when a rod fixed at the lower or upper end is also to be fixed in its centre portion via additional hooks. For implantation technique reasons previous introduction of hooks additionally attached to the rod is not possible.

We claim:

1. An implantable back device comprising in operable communication:

(a) a turnbuckle having a central longitudinal axis with a first bolt and a second bolt extending in opposite directions therefrom along said axis and movable along said axis, said first bolt and said second bolt each having at least one toothed face facing in a direction perpendicular to said axis and rotatable with respect thereto;

(b) at least a first pedicle screw and a second pedicle screw, each having a threaded first end and a second end, wherein said second end of said first and second pedicle screws has at least one toothed face to be interfaced with and clamped to a respective toothed face of either said first bolt or said second bolt; and (c) a clamping means for clamping together said toothed face of a pedicle screw and said toothed face of a bolt of said turnbuckle.

2. Support device according to claim 1, wherein the clamping surfaces of the bolts are traversed by bores and the securing means comprises a screw bolt passing through the bores.

3. Support device according to claim 1, wherein the threaded sleeve comprises spanner faces.

4. Support device according to claim 1, and including also a plurality of locking means cooperating with the threaded bolts and the sleeve for fixing the axial and rotational position of said sleeve and said threaded bolts with respect to each other.

5. Support device according to claim 4, wherein a lock nut is mounted on the threaded shank of the threaded bolts.

6. Support device according to claim 4, wherein a sleeve is deformable by squeezing and at least one flattening on the portion of the bolt is mounted in the sleeve.

7. Support device according to claim 4, wherein the sleeve is at least partially slit and associated with the sleeve is a clamping means for fixedly clamping the sleeve on at least one bolt.

8. Support device according to claim 4, wherein the threaded bolt comprises at least one flattening and between the lock nut and threaded sleeve a washer is mounted non-rotatably on the threaded bolt and comprises an end-face toothing which cooperates with an end-face toothing of the threaded sleeve.

9. Support device according to claim 8, wherein the clamping faces are circular.

10. Support device according to claim 8, wherein between the head and the threaded shank of the pedicle screws a smooth cylindrical portion is provided.

11. Support device according to claim 8, wherein the threaded shank of the pedicle screws comprises a conical core tapering towards the free end.

12. Support device according to claim 8, wherein the head of the screw bolt is conical and cooperates with a conical bore portion of the pedicle screws or threaded bolts.

13. Support device according to claim 12, wherein the bore of the pedicle screws is double-conical.

14. Support device according to claim 12, wherein the screw bolt head has sunken spanner or key faces.

15. Support device according to claim 14, wherein a bolt shank is provided with a blind bore for receiving a preferably cylindrical pin of a relatively long rod which is provided at the other end with holding means for a connecting member to be attached to a vertebra.

16. Support device according to claim 14, wherein the sleeve comprises an insert bore for receiving a preferably cylindrical pin of a relatively long rod which is provided at one end with holding means for a connecting member to be attached to a vertebra.

17. Support device according to claim 14, wherein an adapter which comprises at one end a clamping surface for connection with a bolt and/or a pedicle screw by means of the screw connection and a fork portion spaced from the clamping surface for receiving an elongated preferably threaded rod, the axis of the rod lying in a plane offset with the axis of the bolt and the rod being lockable by means of nuts on the adapter.

18. Support device according to claim 14, wherein at least one separate relatively long bolt is provided having a head with a clamping surface and holding means at the other end for a connecting member to be attached to a vertebra.

19. Device according to claim 18, wherein hook is provided which comprises a holding portion having a through bore through which a rod is led and the holding portion can be secured by means of a locking screw on the rod.

20. Device according to claim 19, wherein the end of the hook is made fork-shaped.

21. Device according to claim 19, wherein a plate, bordering the hook opening on the one side, extends from the holding portion parallel to the axis of the bore and comprises at least one bore for a bone screw.

22. Device according to claim 18, wherein a hook is provided comprising an annular clamping head for securing to the clamping head of a pedicle screw.

23. Device according to claim 18, wherein the rod is engaged laterally by a hook which is attached to an approximately rectilinear holding portion and at the free end of the holding portion laterally on the side opposite the hook an annular clamping surface is disposed.

24. Device according to claim 18, wherein the rod is engaged laterally by a hook which is attached to an approximately rectilinear holding portion and comprises beneath the holding portion at least one bore for a bone screw, the holding portion possibly serving to secure a lamina or pedicle hook.

25. Device according to claim 18, wherein a double hook for the lateral gripping of two rods extending spaced apart adjacent each other and the hooks can be fixed at variable distance from each other.

26. Device according to claim 25, wherein a straight holding portion of the hook comprises a thread on which the second hook is displaceably guided and by means of a nut is restricted in lateral movement towards the free end of the holding portion.

27. Device according to claim 25, wherein the holding portions of the two hooks cooperate telescopically and can be fixed with respect to each other by press deformation.

28. A device according to claim 1, wherein said clamping means comprises a screw bolt and wherein said toothed face of said pedicle screw and said toothed face of said bolt of said turnbuckle are traversed by bores through which said screw bolt can pass.

29. A device according to claim 28, wherein said first pedicle screw and said second pedicle screw each have a first toothed face and a second toothed face.

* * * * *